United States Patent [19]

Nicholson

[11] Patent Number: 4,883,062

[45] Date of Patent: Nov. 28, 1989

[54] TEMPERTURE AND PRESSURE MONITORS UTILIZING INTERFERENCE FILTERS

[75] Inventor: Warren B. Nicholson, Worthington, Ohio

[73] Assignee: Medex, Inc., Hilliard, Ohio

[21] Appl. No.: 186,086

[22] Filed: Apr. 25, 1988

[51] Int. Cl.⁴ .............................................. A61B 5/02
[52] U.S. Cl. ..................................... 128/667; 128/675; 128/736; 128/748
[58] Field of Search ............................. 128/633–634, 128/644–667, 673, 675, 748, 736, 679–701; 73/705, 708, 715; 356/39–42

[56] References Cited

U.S. PATENT DOCUMENTS

| | | | |
|---|---|---|---|
| 3,822,695 | 7/1974 | Takayama | 128/634 |
| 4,114,604 | 9/1978 | Shaw et al. | 128/634 |
| 4,201,222 | 5/1980 | Haase | 128/634 |
| 4,593,701 | 6/1986 | Kobayashi et al. | 128/634 X |
| 4,641,658 | 2/1987 | Lepper | 128/634 X |
| 4,691,709 | 9/1987 | Cohen | 128/667 |
| 4,727,730 | 3/1988 | Boiarski et al. | |

OTHER PUBLICATIONS

Ealing Electro-Optics Company Product Guide 1987-88, pp. 220-223, Interference Filters.

Primary Examiner—Angela D. Sykes
Attorney, Agent, or Firm—Wood, Herron & Evans

[57] ABSTRACT

An interference edge filter is mounted on the end of an optical fiber to provide a sensor for pressure or temperature. The filter is formed such that the transition slope of the filter curve will move to the left or right depending upon the changes in the parameter being monitored. The shift in the position of the slope of the edge filter curve is detected by passing the reflected light through an interference bandpass filter having an edge slope intersecting the transition slope and measuring the intensity of the light passing the bandpass filter.

5 Claims, 2 Drawing Sheets ic
TEMPERATURE AND PRESSURE MONITORS UTILIZING INTERFERENCE FILTERS

BACKGROUND OF THE INVENTION

This invention relates to a monitor for temperature and pressure utilizing an interference filter, and is particularly related to monitors for blood pressure and temperature.

Three principal types of blood pressure monitors are known. The conventional sphygmomanometer employs a cuff wrapped around a patient's arm with means to inflate the cuff and to measure the pressure that the patient's blood vessels put upon the cuff. This is entirely unsuitable for continuous real time monitoring of the patient's blood pressure. The systems currently employed for continuous real time measurement of a patient's blood pressure require a catheter to be inserted in the patient's blood vessel. The catheter is filled with a saline solution that continuously drips into the patient's body. A pressure transducer is mounted in the tubing that conveys the saline solution to the catheter. The blood pressure transducer converts the fluid pressure in the catheter to an electrical signal proportional to the patient's blood pressure. See application Serial No. 07/072,909, filed July 14, 1987.

A third type of the blood pressure transducer, found more in the literature than in actual practice, involves the insertion into the patient's blood vessel of a pressure sensor, the sensor being connected by optical fibers to apparatus for converting the output from the sensor to blood pressure units. The sensor generally is some type of mechanical device or diaphragm that flexes with changes of pressure and the amount of flexure is somehow measured using the optical system. See Boiarski, U.S. Pat. No. 4,727,730, issued Mar. 1, 1988.

Of the three systems described above, the first does not produce real time continuous monitoring. The third has not enjoyed any commercial success. The second, while in widespread use, is expensive and somewhat cumbersome, requiring both the supply of saline solution and a system of stopcocks and flush devices as well as the transducer that is mounted in the fluid system.

An objective of the present invention has been to provide a very simple and inexpensive blood pressure monitor.

Monitoring of temperature presents different problems. The mouth or rectal thermometer is of course well known. It is not useful for providing continuous real time monitoring.

A thermocouple has been used. The problem with the thermocouple is that it is difficult to maintain an electrical isolation of the patient, and there is, therefore, the possibility of heart fibrilation arising out of the use of the thermocouple.

SUMMARY OF THE INVENTION

An objective of the present invention has been to provide an improved simple and inexpensive temperature monitor.

The objectives of providing improved temperature and pressure monitors are attained in part in the same way. An interference filter is mounted on the end of an optical fiber, the interference filter being formed of temperature-responsive elements or pressure-responsive elements for a temperature or pressure sensor, respectively. Optical and electrical circuits are provided to interrogate the sensor and to provide a readout that reflects the parameter (temperature or pressure) being monitored. The interrogation can be continuous and thus produces real time monitoring. The optical fiber provides electrical isolation.

The interference filter is a known device consisting of alternating metal-dielectric-metal layers. Two basic types exist:

Bandpass filters which transmit light only within a defined spectral band ranging from less than one to many nanometers wide; and Edge filters which transmit only above or below a certain "cut on" or "cut off" wavelength and continue to transmit efficiently throughout that range until reaching the transmission limits of the substrate material.

Normally, an effort is made to construct the filter layers in such a manner as to make them as insensitive to temperature variations as possible. The present invention, however, utilizes the known temperature effects on the filter's performance in the following way:

An edge filter produces an intensity versus wavelength curve having a relatively steep slope that defines the wavelengths at which the filter transmits and reflects. That transition line between the transmissive and reflective states will shift depending upon changes of temperature. It is that shift that the present invention measures.

The pressure sensor similarly relies on an edge filter whose transition line between reflective and transmissive states shifts, depending upon the pressure to which the filter is subjected.

The objects of the invention are further attained by providing an optical system wherein the edge filter at the end of an optical fiber is subjected to a polychromatic light. The light reflected from the edge filter is split into two paths with beam splitter. One path is passed through a bandpass filter whose pass band lies under the edge filter curve. The intensity of light in that path should remain constant. The other path is passed through a band pass filter presenting a transmission curve having a slope that intersects the transition slope of the edge filter. The intensity of the transmission through that filter is a measure of the parameter (pressure or temperature) being measured. The ratio of that intensity to the intensity of transmission through the first reference path provides an accurate measure of the parameter that is, through the use of the reference beam, independent of any variables in the system.

There are a number of advantages to the invention. The sensor itself can be relatively easily manufactured by simultaneously forming the edge filter on the ends of a bundle of fibers that have been cut and polished as a unit. Once the layering to form the edge filter is done on the bundle of fibers, the fibers can be individually separated and each becomes a sensor at the end of an optical fiber.

The sensor, on the end of the fiber that is, for example 0.004 inch in diameter, is tiny and could become part of a group of fibers each being inserted into the patient's blood vessel to monitor a specific parameter, e.g., temperature, pressure, blood gas pressures and pH.

BRIEF DESCRIPTION OF THE DRAWINGS

The several features and objectives of the present invention will become more readily apparent conjunction with the accompanying drawings in which.

DESCRIPTION OF THE PREFERRED EMBODIMENTS

Figure 1:
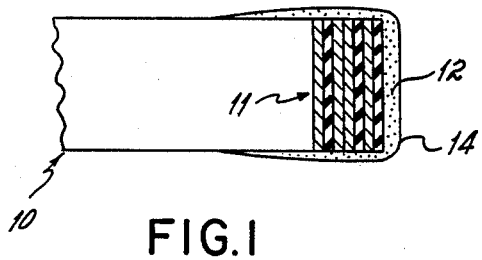
FIG. 1 is a diagrammatic view of an edge filter mounted on an optical fiber to form a sensor.

Referring to FIG. 1, an optical fiber 10 has an edge filter 11 formed on it. The edge filter consists of alternating layers of dielectric and metal or metal coatings. If the edge filter is to be a temperature sensor, one or more of the layers must be dimensionally unstable as to temperature. If the edge filter is to be a pressure sensor, one of the layers must be dimensionally unstable as to pressure variations. These filters are described generally in the section "Interference Filters" of the *Ealing Electro-Optics Catalog*, published by Ealing Electro-Optics, Inc. That catalog description references "applied optics and optical engineering" published by Academic Press for further detailed information. The filter is preferably surrounded by an absorbance layer 12 formed of highly optical absorbent material such as carbon black. A moisture barrier 14 surrounds the absorbance layer and protects the sensitive elements from liquid directly contacting the sensor.

Figure 2:
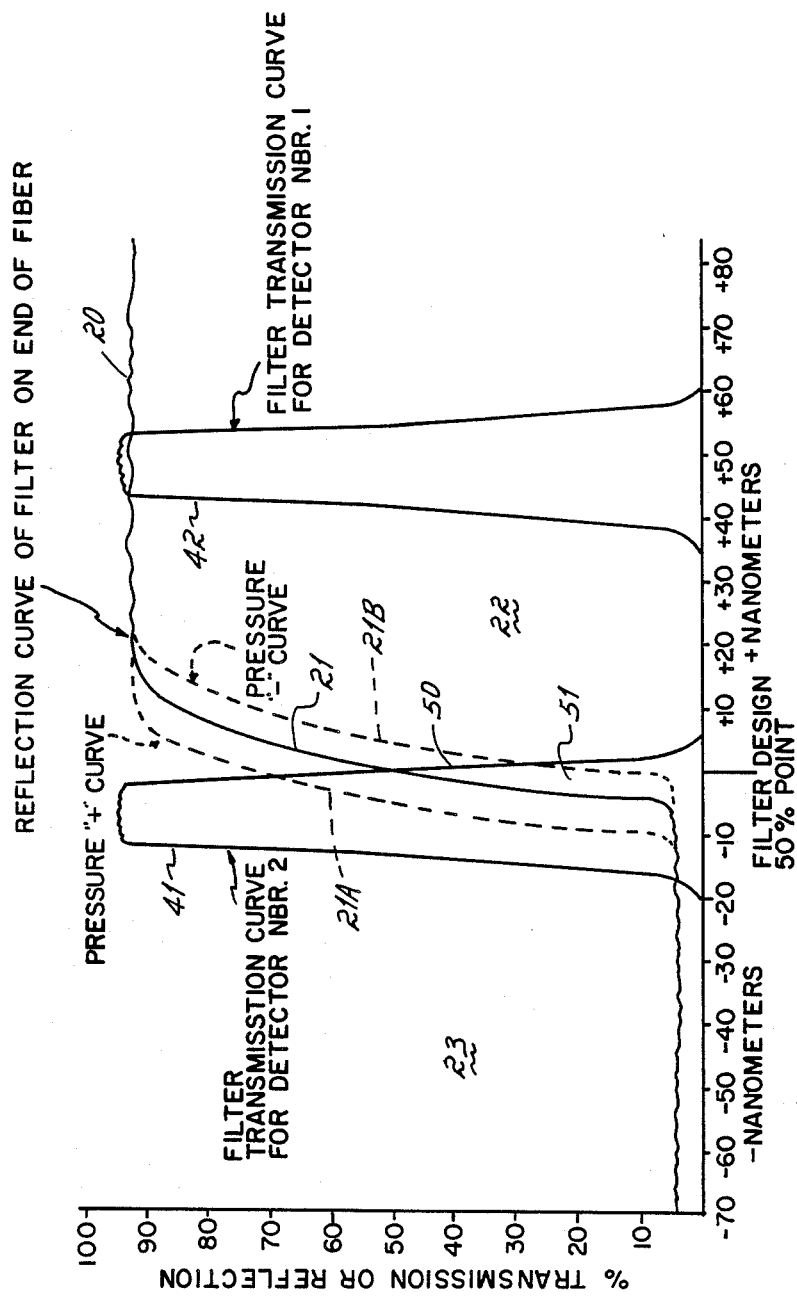
FIG. 2 is a diagrammatic view of an exemplary group of curves for the filters employed in the present invention.

When a polychromatic light is launched through the optical fiber 10, the reflected light will have an intensity versus wavelength curve as shown at 20 in FIG. 2. That curve has a relatively sharp transition line 21 between the wavelengths that are reflected, as delineated by the portion under the curve at 22, and the wavelengths that are transmitted into the absorbance layer as delineated by the area outside the curve at 23. That slope 21 will move to the left as indicated at 21A or to the right as indicated at 21B depending upon the change in the parameter (pressure or temperature) to which the interference filter is sensitive. It is that change of position and the amount of it that provides the measurement of the parameter.

Figure 3:
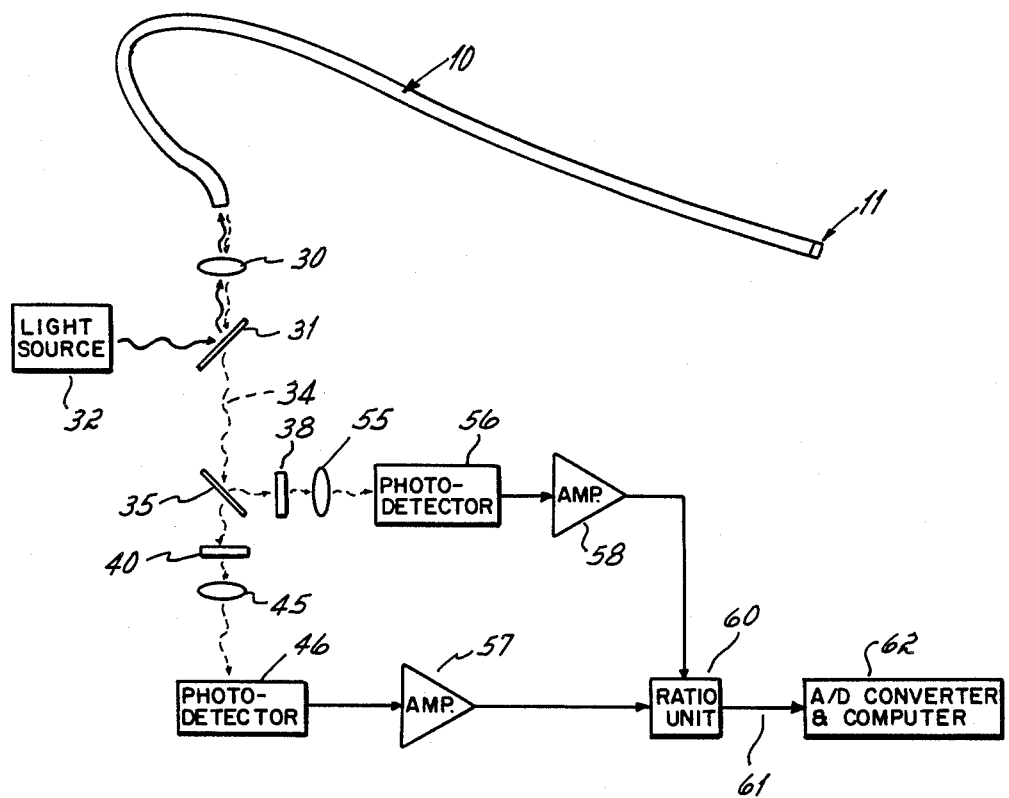
FIG. 3 is an optical and electrical circuit diagram of apparatus employing the present invention.

The apparatus for measuring the change in position is diagrammatically depicted in FIG. 3. Referring to FIG. 3, the optical fiber 10 with the edge filter sensor 11 is connected through a lens 30 and a beam splitter 31 to a polychromatic light source 32. The polychromatic light passes into and is reflected back from the sensor 11, the curve of the reflected light being that shown at 20 in FIG. 2. That reflected beam indicated at 34 strikes a beam splitter 35 that reflects about half of the light toward a narrow band transmission interference filter 38. The remaining portion passes through the beam splitter 35 and is directed to a second narrow band transmission interference filter 40. The transmission curve for the filter 38 is shown at 41 in FIG. 2 and the transmission curve for the filter 40 is shown at 42 in FIG. 2. The portion of the beam passing through the filter 40 is a reference beam. It is directed through a lens 45 to a photodetector 46 that generates an output voltage proportional to the intensity of the light striking the photodetector. Since the reference curve 42 is well under the curve 20 of the reflected light, the intensity of that curve should not change except for variations in the system such as the intensity of the light from the source 32, dust on the lenses, beam splitters, and the like.

The filter 38 is precisely selected so as to provide a transmission curve having a slope 50 that intersects the slope 21. Since the edge filter 11 reflects only the wavelengths under the curve 20, and since the filter 38 passes only the wavelengths under the curve 41, the area defined by the portions below the intersection of the two transition lines 21 and slope 50, as indicated at 51, defines the intensity of the transmission through the filter 38. That beam is focused by a lens 55 onto a photodetector 56 that generates an output voltage proportional to the intensity of the light impinging on the photodetector. The voltages from the respective photodetectors 46 and 56 are fed through amplifiers 57 and 58, respectively, to a ratio unit 60 that provides an output proportional to the ratio of the two inputs, that output being directly proportional to the parameter that is being monitored. That signal indicated at 61 is fed to an output display or analog-to-digital converter and computer indicated at 62.

By referring to FIG. 3, it can be seen that if the parameter being monitored causes the slope 21 to shift to the left, a greater area 51 corresponding to a greater intensity of light will be passed through the filter 38 to impact on the photodetector 56. That greater intensity will be indicative of a change in the parameter being monitored. Similarly, when the slope 21 shifts to the right, the area 51 encompassed by the two curves shrinks and a much lower level of intensity impacts the photodetector 56.

While the invention has been described in relation to an interference filter at the end of an optical fiber, the polychromatic light being reflected from it, it should be understood that light transmitted through the edge filter could be employed. For example, a loop of optical fiber could be provided with the edge filter disposed intermediate the ends of the loop. The polychromatic light would be launched into one end of the loop and received at the other end of the loop. Such a system would be more suitable for monitoring parameters other than blood pressure and temperature since it is not feasible to insert such a loop into patient's blood vessel.

From the foregoing, it can be understood that the present invention has application to the measurement of parameters in environments other than human blood.

From the above disclosure of the general principles of the present invention and the preceding detailed description of a preferred embodiment, those skilled in the art will readily comprehend the various modifications to which the present invention is susceptible. Therefore, I desire to be limited only by the scope of the following claims and equivalents thereof:

I claim:

1. Apparatus for measuring a parameter of blood comprising, an optical fiber having at its end an edge filter consisting of alternating metal and dielectric layers, the layers being dimensionally variable in the presence of the blood parameter to be measured, means for launching a polychromatic light into the end of said optical fiber to produce a reflected light having an intensity versus wavelength reflection curve whose transition line shifts with variations in said blood parameter, means for measuring the amount of the shift of the edge of the reflected curve and means for converting the magnitude of said shift to units of said parameter.

2. Apparatus as in claim 1 in which said measuring means comprises a narrow band transmission interference filter whose passband encompasses at least a portion of said edge of said reflected curve, said filter being in the path of said reflected light intensity of light passing through said filter varying with the position of the edge of said curve.

3. Apparatus as in claim 2 in which said measuring means further comprises a reference narrow band transmission filter having a passband under said reflection curve that does not vary irrespective of shifts in said edge curve, means for splitting said reflected light and passing a first portion through said first filter and passing a second portion through said reference filter, and said converting means including means for comparing the intensity of light passing through said first filter to the intensity of light passing through said reference filter.

4. The method of measuring a parameter of blood comprising the steps of exposing a dimensionally unstable edge filter to the blood, subjecting said filter to polychromatic light to create an intensity versus wavelength curve having a sloping transition line, measuring variations in th position of the transition line of said curve and converting said measured variations to units of said parameter of said blood.

5. The method as in claim 4 further comprising the step of passing the filtered light through a narrow band transmission interference filter having a passband that encompasses a portion of the transition line of said curve, and measuring the intensity of the light passing through said narrow band filter.

* * * * *